United States Patent
Bayerle et al.

(10) Patent No.: US 6,877,354 B2
(45) Date of Patent: *Apr. 12, 2005

(54) METHOD FOR BALANCING OZONE SENSORS

(75) Inventors: Klaus Bayerle, Obertraubling (DE); Frank Hacker, Regensburg (DE); Hong Zhang, Tegernheim (DE)

(73) Assignee: Siemens Aktiengesellschaft, Munich (DE)

( * ) Notice: Subject to any disclaimer, the term of this patent is extended or adjusted under 35 U.S.C. 154(b) by 93 days.

This patent is subject to a terminal disclaimer.

(21) Appl. No.: 10/327,275

(22) Filed: Dec. 20, 2002

(65) Prior Publication Data

US 2003/0131650 A1 Jul. 17, 2003

(30) Foreign Application Priority Data

Dec. 27, 2001 (DE) .......................................... 101 64 179

(51) Int. Cl.⁷ .......................... F01N 11/00; G01N 27/00; G01M 15/00
(52) U.S. Cl. ............................ 73/1.06; 60/277; 702/90; 702/100; 702/104
(58) Field of Search ................................ 73/1.06–1.07, 73/118.1; 701/34, 101–102, 114; 702/90–91, 100, 104, 116; 60/273–274, 276–277

(56) References Cited

U.S. PATENT DOCUMENTS

| | | | |
|---|---|---|---|
| 6,200,542 B1 | 3/2001 | Poles et al. | 423/210 |
| 6,682,638 B1 * | 1/2004 | Prohaska et al. | 204/426 |
| 6,684,629 B2 * | 2/2004 | Bayerle et al. | 60/277 |
| 2002/0110916 A1 * | 8/2002 | Fleischer et al. | 436/37 |

FOREIGN PATENT DOCUMENTS

| | | | | |
|---|---|---|---|---|
| DE | 199 24 083 A1 | 12/2000 | ......... | G01N/27/407 |
| WO | WO 01/91890 A1 | 5/2001 | ........... | B01D/53/86 |

OTHER PUBLICATIONS

SAE Technical Paper Series, "PremAir® Catalyst System—OBD Concepts", Ronald M. Heck, Fred M. Allen, Jeffrey B. Hoke and Ziaolin Yang, Mar. 5–8, 2001, 7 pages.

* cited by examiner

Primary Examiner—Thomas P. Noland
(74) Attorney, Agent, or Firm—David M. Thimmig; Mayer, Brown, Rowe & Maw LLP

(57) ABSTRACT

To balance ozone sensors for the onboard diagnosis of a catalytic element which is arranged in a vehicle and is exposed to an ambient airstream, for breaking down ozone, predetermined enable conditions allowing the sensor balancing to be carried out are checked, and if the enable conditions are fulfilled the values of the output signals from the ozone sensors are recorded and compared with one another. This comparison gives a deviation value which is characteristic of the deviation between the two values, and the deviation value is used to decide whether sensor balancing is required and indeed possible. If sensor balancing is required and possible, the values of the output signals from the ozone sensors are compared with a threshold value and depending on the result of this comparison either an additive or a multiplicative correction of the values of the output signals is performed.

11 Claims, 2 Drawing Sheets

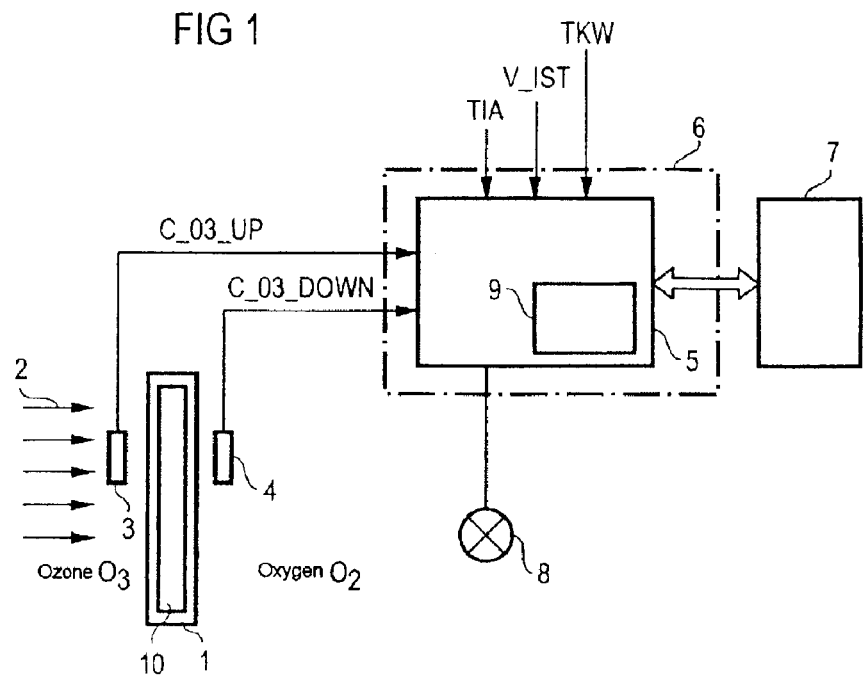

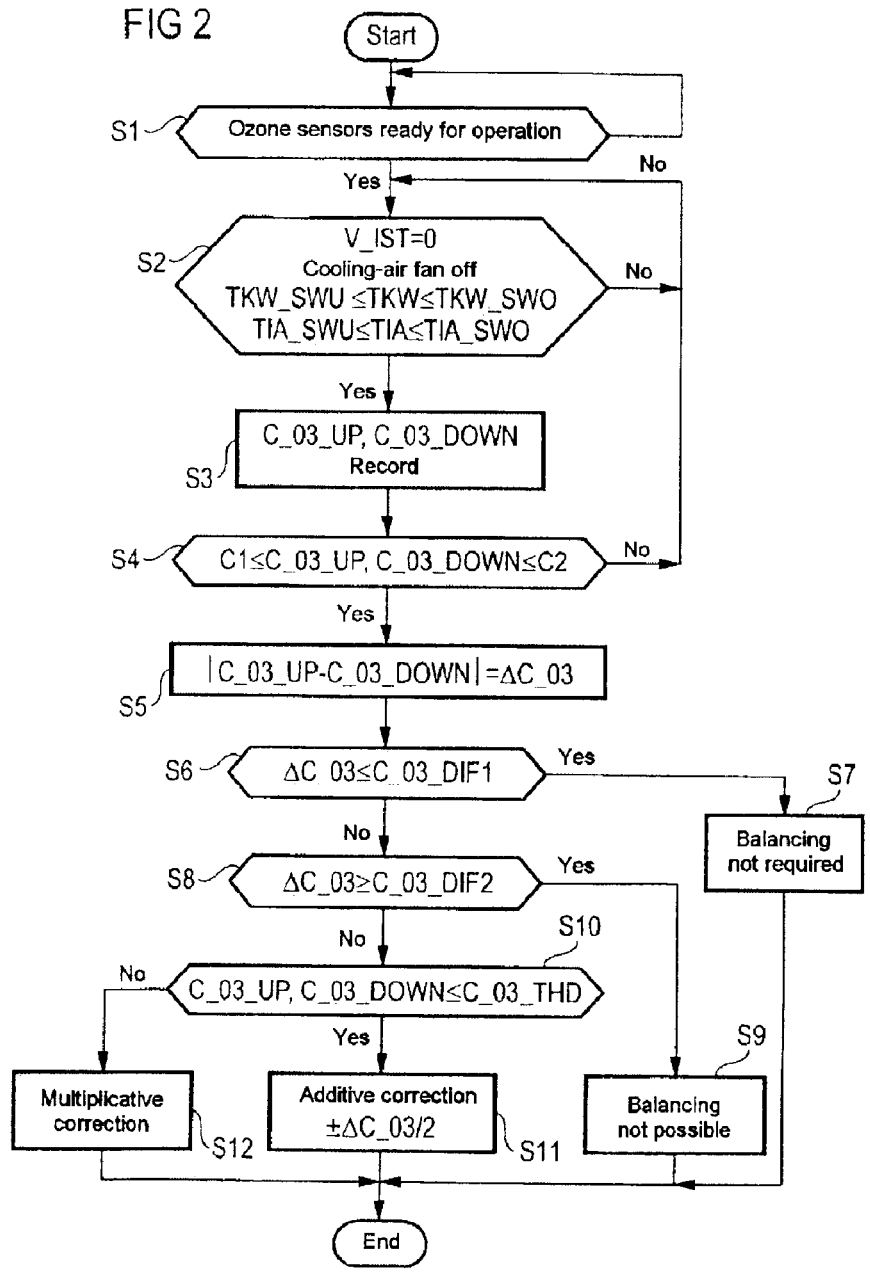

METHOD FOR BALANCING OZONE SENSORS

BACKGROUND OF THE INVENTION

The invention relates to a method for balancing ozone sensors for the onboard diagnosis of a catalytic element for breaking down ozone in a vehicle.

For reasons for environmental and personal protection, the levels of pollution which result from vehicles with internal combustion engines or from the generation of power using stationary combustion installations needs to be reduced significantly.

A novel approach aimed at reducing pollution consists in actively removing pollutants not directly from the exhaust-gas stream from an internal combustion engine or a stationary combustion installation, but rather from the ambient air. This route is particularly promising for the removal of ground-level ozone, which has a considerable effect on human health on account of its strongly oxidizing action. Ozone itself is not a gas which is emitted directly and therefore cannot be removed from the exhaust-gas stream. It is formed when nitrogen oxides are present in outside air under insolation, on account of the UV content thereof, as a result of complex photochemical reaction equilibria.

Since ozone is extremely reactive, it can be successfully broken down quantitatively by means of a catalytic converter system through which air flows. These catalytic converters are extremely stable, since there is no need for any direct action from strong oxidation catalytic converters, which are highly sensitive to poisoning, such as for example platinum. Systems which substantially cause adsorption of the ozone on a surface are sufficient to achieve this effect; the ozone then breaks down instantaneously to form oxygen.

Such catalytic converter systems have long been in use in passenger aircraft which fly close to the ozone layer. There, they are used to treat the air which is passed into the passenger compartment. Recently, such systems have also been used in motor vehicles. In this case, the radiator of the vehicle is coated with the catalyst. The air, which flows in large quantities through the radiator, has ozone quantitatively removed from it, i.e. the vehicle purifies the ambient air.

When ozone catalyst systems of this type are used, the American environmental authority CARB (California Air Resources Board) grants automobile manufacturers credits relating to the exhaust-gas limits for the LEV (Low Emmission Vehicle) exhaust legislation. However, credits are only granted if there is onboard diagnosis of the ozone catalyst system.

A system of this type is described in the publication SAE Paper 2001-01-1302 "PremAir® Catalyst System—OBD Concepts", Ronald M. Heck, Fred M. Allen, Jeffrey B. Hoke and Xiaolin Yang; Engelhard Corporation.

DE 199 24 083 A1 describes a conductivity sensor for-the detection of ozone which, by combining the semiconductor materials gallium oxide and indium oxide ($Ga_2O_3$, $In_2O_3$), on the one hand exploits the strong ozone sensitivity of indium oxide and on the other hand exploits the stable and reproducible conductivity properties of gallium oxide.

On account of the use of a plurality of, in particular two, sensors, the properties of which are only identical in an ideal scenario, for diagnosis, it is necessary to reckon with inaccuracies in the determination of the ozone concentration on account of the sensor specification and sensor aging. To minimize this influence and therefore to allow reliable diagnosis of the ozone conversion, the sensors have to be balanced or their output signals have to the checked for plausibility.

The invention is based on the object of providing a method for balancing ozone sensors for the onboard diagnosis of a catalytic element for breaking down ozone in a vehicle.

This object is achieved as described in the features of the invention in the claims.

SUMMARY OF THE INVENTION

The method according to the invention is distinguished by the fact that, to balance ozone sensors (3, 4) for the onboard diagnosis of a catalytic element (10), which is arranged in a vehicle and is exposed to an ambient airstream, for breaking down ozone, predetermined enable conditions allowing the sensor balancing to be carried out are checked, and if the enable conditions are fulfilled, the values of the output signals (C_03_UP, C_03_DOWN) from the ozone sensors (3, 4) are recorded and compared with one another. This comparison gives a deviation value (ΔC_03), which is characteristic of the deviation between the two values, and this deviation value (ΔC_03) is used to decide whether sensor balancing is required and indeed possible.

If sensor balancing is required and possible, the values of the output signals ((C_03_UP, C 03_DOWN) from the ozone sensors (3, 4) are compared with a threshold value (C_03_THD), and depending on the result of this comparison either an additive or a multiplicative correction of the values of the output signals (C_03_UP, C_03_DOWN) is performed.

BRIEF DESCRIPTION OF THE DRAWINGS

The invention is explained in more detail below on the basis of an exemplary embodiment and with the aid of figures, in which:

FIG. 1 shows an outline illustration showing how to check the conversion capacity of a radiator, which is coated with a catalytic element, of a vehicle.

FIG. 2 shows a flow diagram relating to the balancing of ozone sensors for the onboard diagnosis of a catalytic element for breaking down ozone in a vehicle.

DETAILED DESCRIPTION OF THE PREFERRED EMBODIMENT

In the illustration shown in FIG. 1, an ambient airstream 2 flows onto a radiator 1 of a vehicle. The incoming flow is produced by the speed of the vehicle, by the slipstream and/or by a radiator fan (not shown). The radiator 1 is coated with a catalytic element 10 for breaking down ozone, referred to below as the ozone catalyst. A first ozone sensor 3 for determining the ozone concentration in the ambient air upstream of the radiator 1 is arranged upstream of the radiator 1. The signal from the ozone sensor 3 is denoted by C_03_UP. A second ozone sensor 4 for determining the ozone concentration in the ambient air downstream of the radiator 1 is arranged downstream of the radiator 1. The signal from the ozone sensor 4 is denoted by C_03_DOWN.

Both ozone sensors 3, 4 are connected to, a control and evaluation device 5 which evaluates the measured values C_03_UP, C_03_DOWN from the two ozone sensors 3, 4. This device is preferably designed as a microprocessor. The control and evaluation device 5 may also be integrated in an engine management unit 6 which controls operation of the internal combustion engine of the vehicle, as indicated by dot-dashed lines in FIG. 1. Further operating variables of the internal combustion engine and environmental parameters, in particular the actual value of the vehicle speed V_IST, the coolant temperature TKW of the internal combustion engine driving the vehicle and the ambient air temperature TIA, are fed to the control and evaluation device 5.

The control and evaluation device has a fault memory 9, in which the results of the check of the conversion capacity of the ozone catalyst are stored.

Furthermore, the control and evaluation device 5 is connected to a memory device 7, in which various characteristic diagrams and threshold values, the importance of which will be explained below, are stored. In particular, the relationship between the output signal from the ozone sensor—generally an electric voltage—and the ozone concentration in ppb (parts per billion) is stored in a characteristic diagram.

Moreover, the control and evaluation device 5 controls a display means 8, which indicates to the driver of the vehicle whether the ozone conversion is functioning correctly. If the conversion rate is below a predetermined value, by way of example a warning light can light up or an acoustic signal can be generated. It is also possible for the current conversion rate to be displayed continuously.

The flow diagram illustrated in FIG. 2 shows a method for balancing the two ozone sensors 3, 4.

After the diagnosis has started, in a first method step S1 it is checked whether the two ozone sensors 3, 4 are ready for operation. To obtain reproducible signals from the ozone sensors 3, 4, the sensor elements of the sensors 3, 4 have to be brought to their operating temperature. This is achieved by means of an electrical heating device which is controlled by means of signals from the control and evaluation device 5 (FIG. 1). If ozone sensors based on semiconducting metal oxides whose sensitive materials consist, for example, of pure indium oxide ($In_2O_3$) are used, an operating temperature of approx. 500° C. is required.

If at least one of the two ozone sensors 3, 4 is not yet ready for operation, the methods step S1 is run again until the check gives a positive result (waiting loop).

If both ozone sensors 3, 4 are ready for operation, method step S2 checks whether preset conditions for the balancing of the two ozone sensors 3, 4 are fulfilled.

Firstly, there must be no flow through the catalytic element 10 of the radiator 1. For this purpose, first of all it is checked whether the actual speed V_IST of the vehicle is equal to zero. Since speeds of exactly V_IST=0 can only be recorded with a relatively high level of outlay, vehicle speeds which are greater than zero but below a defined, predetermined limit value (e.g. 1.8 km/h) are treated as a signal for V_IST=0 and are therefore no guarantee that the vehicle is completely stationary. However, the flow through the catalytic element 10 of the radiator 1 is then negligible. The cooling-air fan must also be switched off.

Furthermore, method step S2 checks whether the coolant temperature TKW lies within a range which is limited by a lower threshold value TKW_SWU and an upper threshold value TKW_SWO and whether the intake air temperature TIA lies within a range which is limited by a lower threshold value TIA_SWU and an upper threshold value TIA_SWO. If just one of the abovementioned conditions is not fulfilled, method step S2 is run again until these checks give a positive result (waiting loop). These temperature checks are required since ozone only exists at certain temperatures and therefore balancing of the ozone sensors 3, 4 only gives a useful result at certain temperatures.

If the abovementioned conditions are all fulfilled, in a method step S3 the current values of the output signals C_03_UP and C_03_DOWN from the two ozone sensors 3, 4 are read by the control and evaluation unit 5, and each value is independently compared with a lower threshold value C1 and an upper threshold value C2 in method step S4. This checks whether the two sensor signals are identical within a certain tolerance. The threshold values (constants) are dependent on the type of sensors used, in particular on the nominal characteristic curve of the ozone sensors 3, 4 used and are stored in the memory device 7.

If both values C_03_UP and C_03_DOWN are within the range defined by the constants C1, C2, a deviation value, defined as the magnitude of the difference $\Delta C\_03$ between the two signals C_03_UP and C_03_DOWN, is formed in a method step S5, or otherwise the method branches back to method step S2.

A method step S6 checks whether the deviation value $\Delta C\_03$ is less than or equal to a predetermined first threshold value C_03_DIF1. This threshold value is stored in the memory device 7. If the result of this check is positive, a method step S7 determines that the two ozone sensors 3, 4 do not need to be balanced, and the method is complete.

If the deviation value $\Delta C\_03$ is greater than the predetermined first threshold value C_03 DIF1, balancing is required, and a method step S8 checks whether the deviation value $\Delta C\_03$ is greater than or equal to a second threshold value C_03_DIF2. If so, a method step S9 determines that balancing is not possible, and it is concluded that there is a fault in one of the two ozone sensors 3, 4 and the method is complete.

If the check carried out in method step S8 reveals that the deviation value $\Delta C\_03$ is lower than the second threshold value C_03_DIF2, the method branches off to a method step S10, where the current values of the output signals C_03_UP and C_03_DOWN from the two ozone sensors 3, 4 are each compared with a threshold value C_03_THD. If the two values are less than or equal to this threshold value C_03_THD, a method step S11 performs an additive correction by adding or subtracting a correction term, which corresponds to half the deviation value $\Delta C_{13}$ 03, to/from the values C_03_UP, C_03_DOWN.

This means that the correction term $\Delta C\_03/2$ is added to the current value of the output signal from that ozone sensor which is showing the lower value, and the correction term $\Delta C\_03/2$ is subtracted from the current value of the output signal from that ozone sensor which is showing the higher value. In this way, the two ozone sensors 3, 4 are balanced and the method is complete.

Therefore, an additive correction takes place if the two values of the sensor signals C_03 UP and C_03_DOWN lie on the approximately linear branch of the sensor characteristic curve.

If the two values C_03 UP, C_03_DOWN are higher than the threshold value C_03_THD (check performed in method step S10), the two values of the sensor signals C_03_UP and C_03 DOWN lie on the nonlinear part of the sensor characteristic curve, and a multiplicative correction is performed in a method step S12.

This is carried out by forming the quotient from the two values (C_03_UP, C_03_DOWN) and multiplying the denominator by the quotient.

In this way, the two ozone sensors 3, 4 are balanced and the method is complete.

The method described is started again each time the engine is started and, to avoid undesirable flow through the radiator, for example on account of a high level of wind, is carried out a number of times during a driving cycle.

What is claimed is:

1. A method for balancing ozone sensors for the onboard diagnosis of a catalytic element, which is arranged in a vehicle and is exposed to an ambient airstream, for breaking down ozone, in which a first ozone sensor is exposed to the ambient airstream upstream of the catalytic element and a second ozone sensor (4) is exposed to the ambient airstream downstream of the catalytic element, the method comprising the steps of:

checking predetermined enable conditions necessary for the sensor balancing to proceed, if the enable conditions are fulfilled, recording output signal values from the first and second ozone sensors, comparing the output signal values with one another, and obtaining a deviation value which is characteristic of the deviation between the two values, using the deviation value to determine whether sensor balancing is required and possible, if sensor balancing is required and possible, comparing the output signal values from the first and second ozone sensors with a threshold value and depending on the comparison result, performing either an additive or a multiplicative correction of the output signal values.

2. The method as claimed in claim 1, further comprising the step of obtaining the deviation value by evaluating the magnitude of the difference between the output signal values from the first and second ozone sensors.

3. The method as claimed in claim 1, further comprising the step of comparing the deviation value with a first threshold value, and determining that sensor balancing is required if the deviation value is below the threshold value.

4. The method as claimed in claim 1, further comprising the step of comparing the deviation value with a second threshold value and determining that sensor balancing is possible if the deviation value is above the threshold value.

5. The method as claimed in claim 1, further comprising the step of performing an additive correction if the output signal values are less than or equal to a threshold value, or performing a multiplicative correction if the output signal values exceed the threshold value.

6. The method as claimed in claim 5, wherein the additive correction is carried out by adding a correction term to the lower of the two output signal values and by subtracting the correction term from the higher of the two output signal values.

7. The method as claimed in claim 6, wherein the correction term corresponds to half the deviation value.

8. The method as claimed in claim 5, wherein the multiplicative correction is carried out by forming a quotient from the two output signal values and multiplying the denominator by the quotient.

9. The method as claimed in claim 1, wherein the enable condition checked is whether vehicle speed is approximately zero.

10. The method as claimed in claim 1, wherein the enable condition checked is whether intake air temperature is above a range limited by an upper and lower threshold value.

11. The method as claimed in claim 1, wherein the enable condition checked is whether coolant temperature is above a range limited by an upper and lower threshold value.

* * * * *